(12) United States Patent
Li

(10) Patent No.: US 9,333,062 B2
(45) Date of Patent: May 10, 2016

(54) BODILY IMPLANTS AND METHODS OF TREATING FECAL INCONTINENCE USING BODILY IMPLANTS

(75) Inventor: Jianmin Li, Lexington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 75 days.

(21) Appl. No.: 13/489,157

(22) Filed: Jun. 5, 2012

(65) Prior Publication Data

US 2012/0316385 A1 Dec. 13, 2012

Related U.S. Application Data

(60) Provisional application No. 61/495,593, filed on Jun. 10, 2011.

(51) Int. Cl.
*A61F 2/02* (2006.01)
*A61F 2/00* (2006.01)

(52) U.S. Cl.
CPC .............. *A61F 2/0036* (2013.01); *A61F 2/0045* (2013.01)

(58) Field of Classification Search
CPC .............................. A61F 2/0036; A61F 2/0045
USPC ................................ 600/29, 30; 128/897–899
See application file for complete search history.

(56) References Cited

U.S. PATENT DOCUMENTS

| 7,588,598 | B2 * | 9/2009 | Delorme et al. | 623/11.11 |
| 7,878,969 | B2 * | 2/2011 | Chu et al. | 600/30 |
| 2005/0043580 | A1 * | 2/2005 | Watschke et al. | 600/30 |
| 2005/0267325 | A1 * | 12/2005 | Bouchier et al. | 600/37 |
| 2006/0041861 | A1 | 2/2006 | Trefler et al. | |
| 2007/0299299 | A1 * | 12/2007 | Rosenblatt | 600/30 |
| 2008/0177132 | A1 * | 7/2008 | Alinsod et al. | 600/37 |
| 2010/0234672 | A1 * | 9/2010 | Weiser et al. | 600/30 |
| 2010/0261952 | A1 * | 10/2010 | Montpetit et al. | 600/37 |
| 2010/0312043 | A1 * | 12/2010 | Goddard | 600/30 |
| 2011/0082328 | A1 * | 4/2011 | Gozzi et al. | 600/30 |
| 2011/0112357 | A1 * | 5/2011 | Chapman et al. | 600/37 |
| 2011/0124954 | A1 * | 5/2011 | Ogdahl et al. | 600/30 |

FOREIGN PATENT DOCUMENTS

| WO | 2008/058163 A2 | 5/2008 |
| WO | 2010/141321 A1 | 12/2010 |
| WO | 2012/170661 A1 | 12/2012 |

OTHER PUBLICATIONS

International Search Report and Written Opinion for International Application No. PCT/US2012/041296, mailed Sep. 17, 2012, 20 pages.
International Preliminary Report on Patentability for International Application No. PCT/US2012/041296, mailed Dec. 27, 2013, 8 pages.

* cited by examiner

*Primary Examiner* — Navin Natnithithadha
*Assistant Examiner* — Sunita Reddy
(74) *Attorney, Agent, or Firm* — Brake Hughes Bellermann LLP

(57) ABSTRACT

A bodily implant is provided that includes a support member and an arm member. The support member is configured to be placed within a body of a patient such that the support member surrounds a rectum of the patient. The arm member extends from the support member and is configured to be coupled to a portion of the body of the patient to help retain the support member in place within the body of the patient.

18 Claims, 17 Drawing Sheets

BODILY IMPLANTS AND METHODS OF TREATING FECAL INCONTINENCE USING BODILY IMPLANTS

CROSS REFERENCE TO RELATED APPLICATION

This application is a Nonprovisional of, and claims priority to, U.S. Provisional Application No. 61/495,593, filed on Jun. 10, 2011, entitled "BODILY IMPLANTS AND METHODS OF TREATING FECAL INCONTINENCE USING BODILY IMPLANTS", which is incorporated by reference herein in its entirety.

BACKGROUND

1. Field

The present invention generally relates to implants and more particularly to bodily implants and their methods of delivery and placement into a patient's body for the treatment of fecal incontinence.

2. Description of the Related Art

Fecal incontinence is a disorder that involves involuntary passage of feces through an anal canal of a patient. The disorder may be caused by weakness or damage to internal and external anal sphincters muscles or levator ani muscles surrounding the anal canal of the patient's body. Usually in a normal human body, the internal and external sphincters and levator ani muscles support a rectum and may help provide the rectum an ano-rectal angle that sustains the feces in the rectum until voluntary defecation. However, as stated previously, weakness or damage to the normal pelvic-support systems causes the ano-rectal angle to distort thereby causing involuntary passage of feces.

Treatment of this problem has centered on pelvic floor rehabilitation, dietary changes, and/or surgical treatments. One of the surgical treatments includes a sling procedure involving placing an implant such as a sling into a patient's body around the anal canal.

Surgical devices and procedures exist that focus on supporting a portion of the rectum by using a bodily implant. For example, the bodily implant may support an anterior portion of the rectum in one case. In another case, the bodily implant may, for example, support posterior portion of the rectum, and the like. The implant is thus configured to surround only a portion around the rectum.

In addition, one or two arms extend from the bodily implant and are tied or coupled to one or more portions of the body tissues, thereby securing the bodily implant with the body tissues. In some embodiments, the one or two arms may not sufficiently distribute tensioning forces around the rectum. In some other embodiments, the implants of partial support of the rectum may not conform to the anatomy and therefore may often lead to incomplete fecal continence. Consequently, the stability of the bodily implant may be reduced and the implant may not function appropriately. Therefore, the current devices and procedures may not sufficiently support the rectum to effectively treat fecal incontinence. Further, the stability of the implant may be a concern with the current designs and structures of the bodily implants.

In accordance with the foregoing, there is a need for a device and a method that facilitates the placement and support of a bodily implant within a body of a patient to treat fecal incontinence.

SUMMARY

A bodily implant is provided that includes a support member and an arm member.

The support member is configured to be placed within a body of a patient such that the support member surrounds a rectum of the patient. The arm member extends from the support member and is configured to be coupled to a portion of the body of the patient to help retain the support member in place within the body of the patient. Such a configuration of the implant may form a support of the rectum and help to prevent feces leaking, regardless of the rectum position/orientation.

BRIEF DESCRIPTION OF THE FIGURES

The invention and the following detailed description of certain embodiments thereof may be understood by reference to the following figures.

DETAILED DESCRIPTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but rather to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "operatively coupled," as used herein, is defined as connected, although not necessarily directly and mechanically.

The present invention relates to bodily implants and methods for their delivery and placement into a patient's body for the treatment of fecal incontinence. In some embodiments, the bodily implants act as anal supports and facilitate in proper tensioning of internal and external anal sphincter muscles or the levator ani muscles surrounding the anal canal to prevent involuntary passage of feces. In some embodiments, the anal support provided by the bodily implants involves formation of a loop structure around the anus. In some embodiments, this loop or ring structure applies a tensioning force to maintain the sphincters or the rectum or the rectal canal of a patient in a position that is more desired for preventing the involuntary passage of feces. In some embodiments, the bodily implants are fixed or retained in place within the body by adjacent scar tissues upon healing.

The term patient may be used for a person who is benefitted of the bodily implants and/or the surgical procedures of the present invention. For example, the patient is a person within whom the bodily implant is delivered and placed. The patient may be a human female, a human male or any other mammal.

The terms proximal and distal described in relation to various devices, apparatuses, and components as discussed in the subsequent text of the present invention are referred with a point of reference. The point of reference, as used in this description, is a perspective of an operator. The operator may be a surgeon, a physician, a nurse, a doctor, a technician, and the like who may perform the procedure of delivery and placement of the bodily implants into the patient's body as described in the present invention. The term proximal refers to an area that is closest to the operator. The term distal refers to an area that is farthest from the operator.

Figure 1:
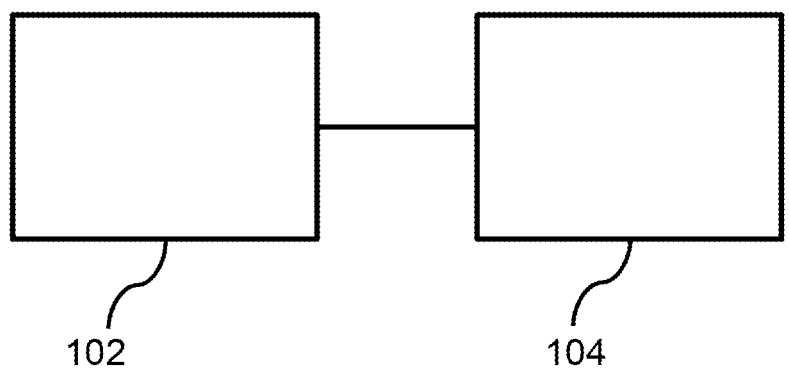
FIG. 1 is a schematic diagram of a bodily implant configured to be delivered into a patient's body for the treatment of fecal incontinence, in accordance with an embodiment of the present invention.

FIG. 1 is a schematic diagram of a bodily implant 100 configured to be delivered into a patient's body for the treatment of fecal incontinence, in accordance with an embodiment of the present invention. The bodily implant 100 may be a sling system that is utilized in the treatment of fecal incontinence. The bodily implant 100 includes a support member 102 and an arm member 104.

The support member or portion 102 is configured to be placed within a patient's body such that the support member 102 surrounds a rectum and/or anus of the patient. In an embodiment, the bodily implant 100 completely surrounds (i.e., form a complete loop or ring around) a portion of the rectum and/or anus of the patient. In another embodiment, the bodily implant 100 partially surrounds a portion of the rectum and/or anus of the patient.

In some embodiments, the support member 102 includes a first coupling portion and a second coupling portion (not shown) such that the first coupling portion is configured to be coupled to the second coupling portion such that the support member 102 forms a ring around the rectum in the body of the patient.

The support member 102 can be of a variety of different shapes, sizes, and configurations depending on the indented use of the bodily implant 100 and location of its placement within the body of the patient. In some embodiments, the support member 102 can be substantially rectangular, square, oval, or elliptical. The support member 102 can be shaped and sized to support the portion of the anal canal or rectum of the patient. In accordance with several embodiments, the support member 102 may be configured to conform to the shape of the body of the patient. For example, the support member 102 may be placed in a ring shape, such as in the shape of an annular ring, to help it conform to the external contour of the rectum, and/or anus.

The arm member 104 extends from the support member 102 and is configured to be coupled to a portion of the body of the patient to help retain the support member 102 in place within the body of the patient. For example, in an embodiment, the arm member 104 is configured to pass through an obturator foramen or extend to the retropubic or suprapubic region of the patient. In some embodiments, the arm member 104 extends from the support member 102 to a location posterior to the anus/rectum of the patient. In other embodiments, the arm member 104 extends from the support member 102 to a location anterior to the anus/rectum of the patient.

In some embodiments, the arm member 104 is removably or fixedly coupled to the support member 102. In other embodiments, the arm member 104 is integrated to the support member 102 such that the support member 102 and the arm member 104 form a single integral structure. The arm member 104 may extend from any location of the support member 102 such that it comfortably supports and retains the support member 102 around the rectum of the patient.

In some embodiments, the support member 102 and the arm member 104 are formed of a material that allows tissue in-growth after implantation. In an embodiment, the support member 102 and the arm member 104 can be made from a biological material or a cadaveric tissue. In another embodiment, the support member 102 and the arm member 104 may be made up of synthetic material such as silastic, polypropylene mesh or other plastic materials, stem cells, natural xenograft material, collagen growth factors, and the like. The synthetic material may be elastic and flexible, which may allow stretching of the bodily implant 100 with abdominal straining. In some embodiments, the support member 102 and the arm member 104 are made of flexible material. In other embodiments, the support member 102 and the arm member 104 are made of elastic material. Additionally, the bodily implant 100 may be coated, impregnated, or formed with one or more drugs to be eluted to an adjacent tissue, in accordance with several other embodiments. In some embodiments, the support member 102 and the arm member 104 are formed of the same material. In certain other embodiments, the support member 102 and the arm member 104 are formed of different materials. For example, the support member 102 can be formed from a first biocompatible material and the arm member 104 can be formed from a second biocompatible material different than the first biocompatible material. In some embodiments, the arm member 104 is elastic and is configured to stretch.

The support member 102 and the arm member 104 can have a variety of sizes (length, width, and thickness) depending on the intended use of a particular bodily implant such as the bodily implant 100 and the intended site of implantation. For example, the size of the support member 102 can depend on the size of the rectum or rectal canal. Similarly, the size of the arm member 104 can have a length such that the support member 102 can be placed through and secured to the surrounding bodily tissues properly. For example, in some embodiments, the arm member 104 may be secured to bodily tissue via stitching, an anchor, or other securement mechanism.

Figure 2:
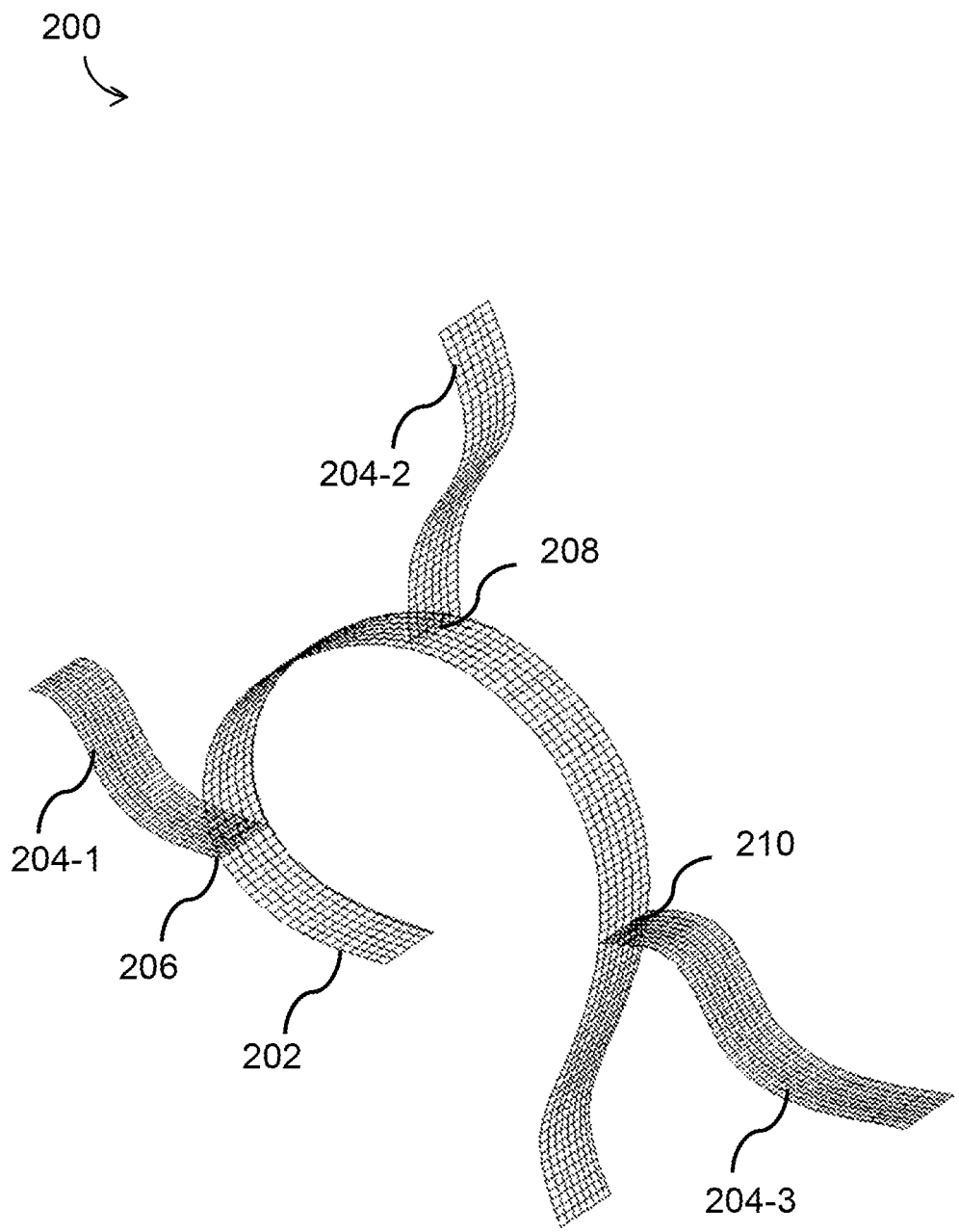
FIG. 2 is a perspective illustration of a bodily implant configured to be delivered into a patient's body for the treatment of fecal incontinence, in accordance with an embodiment of the present invention.

In accordance with several different embodiments, the number of arm members similar to the arm member 104 as utilized and coupled to the support member 102 may vary based on the intended use of the bodily implant 100. For example, in an embodiment, three arm members similar to the arm member 104 may be utilized. In another embodiment, four arm members similar to the arm member 104 may be utilized. In another embodiment, five arms or more than five arms are utilized in the implant. In an embodiment, the arm members such as the arm member 104 are equally spaced along the support member. In other embodiments, the arm members are not equally spaced along the support member FIG. 2 is a perspective illustration of a bodily implant 200 configured to be delivered into a patient's body for the treatment of fecal incontinence, in accordance with an embodiment of the present invention. The bodily implant 200 includes a support member 202 and three arm members 204-1, 204-2, and 204-3, collectively referred to as 204. A first arm member 204-1 extending from the support member 202 at a first location 206 is configured to be coupled to a first portion of the body of the patient to help retain the support member 202 in place within the body of the patient. A second arm member 204-2 extending from the support member 202 at a second location 208 is configured to be coupled to a second portion of the body of the patient to help retain the support member 202 in place within the body of the patient. A third arm member 204-3 extending from the support member 202 at a third location 210 is configured to be coupled to a third portion of the body of the patient to help retain the support member 202 in place within the body of the patient. The three different locations 206, 208, and 210 for coupling the three arm members 204 on the support member 202 are spaced apart by a fixed distance. The fixed distance between the three different locations 206, 208, and 210 may be altered in accordance with various embodiments of the bodily implant 200 and based on the intended site of the implantation. In some embodiments, the support member 202 may also include a first coupling portion and a second coupling portion such that the first coupling portion is configured to be coupled to the second coupling portion. The first and second coupling members could be portions of a snap or button type system. In such embodiments, support member 202 may be inserted into a body of a patient and the first coupling portion may be engaged and coupled to the second coupling portion such that the support member 202 forms a ring or loop around a rectum of the patient. Further, the support member 202 disposed between the three arm members 204 may be structured in a manner such that it may completely surround the rectum. In some embodiments, the support member 202 forms an annular member like structure upon placement within the patient's body that circumferentially surrounds the rectum.

The shapes, sizes and configurations of the bodily implant 200 may vary based on the intended use and the site of the implantation. This has been described in conjunction with FIG. 1 in detail. Further, the bodily implant 200, as illustrated in FIG. 2 may be made of several types of materials described in conjunction with FIG. 1 in detail.

Figure 3:
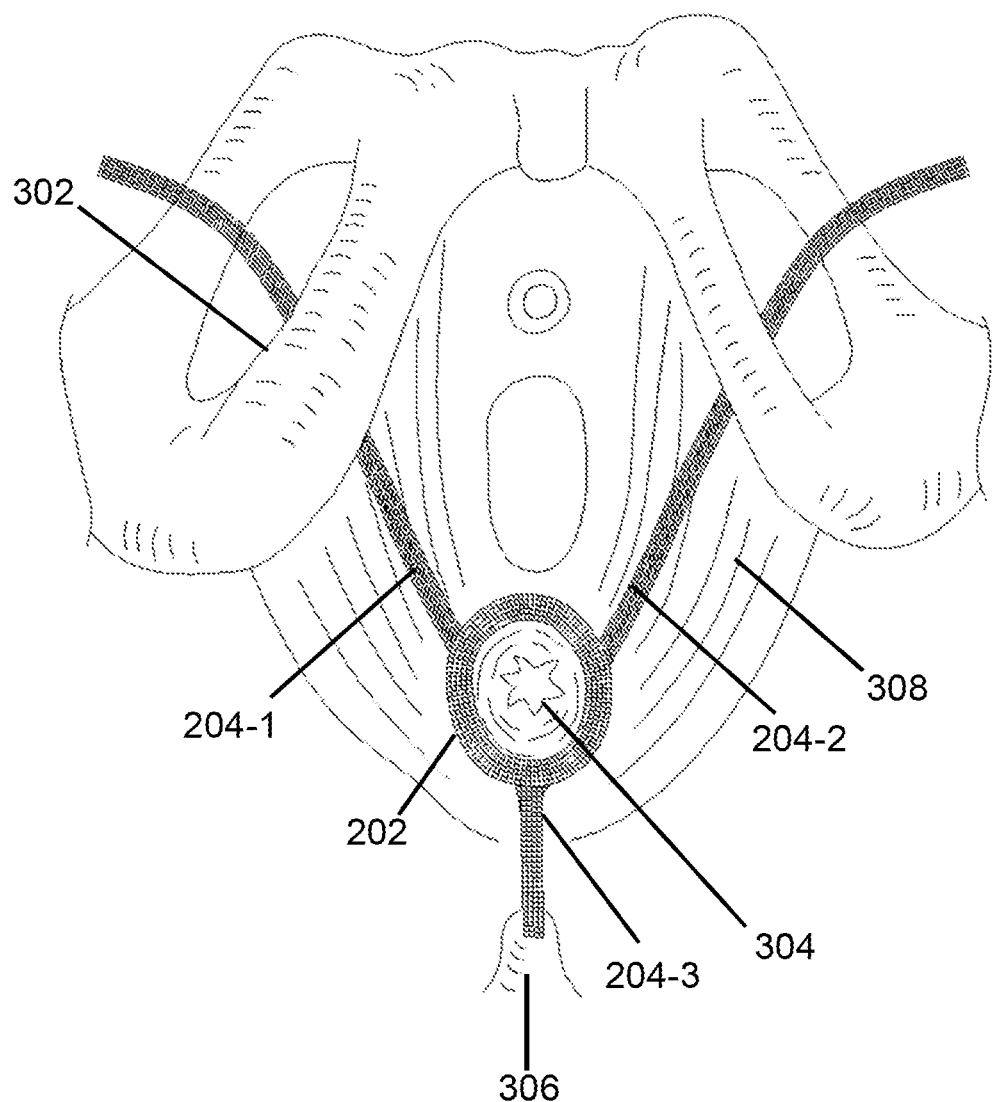
FIG. 3 schematically illustrates the bodily implant of FIG. 2 disposed within a pelvic region of a patient in accordance with an embodiment of the present invention.

FIG. 3 illustrates positioning of a bodily implant such as the bodily implant 200 disposed within a pelvic region of a patient in accordance with an embodiment of the present invention. The bodily implant 200 has been described in conjunction with FIG. 2 in detail. Referring to FIG. 3 now, the anatomy of the pelvic region including an obturator foramen 302, a rectum 304, and a coccyx 306 of the patient is depicted. FIG. 3 also demonstrates the relationship of the levator ani muscles (particularly, the puborectalis 308) to the rectum 304. As shown in FIG. 3, the support member 202 is placed within the body tissues of the patient such that it surrounds the rectum 304 of the patient. Further, as shown in FIG. 3, the three arm members 204 are disposed between the rectum 304 and the coccyx 306, and extend up through the obturator membrane of the obturator foramen 302.

In embodiments, the three arm members 204 may be attached to one or more portions within a body of the patient. The first arm member 204-1 is configured to be coupled to a first portion of the body of the patient to help retain the support member 202 in place within the body of the patient to help retain the support member 202 in place within the body of the patient. The second arm member 204-2 is configured to be coupled to a second portion of the body of the patient to help retain the support member 102 in place within the body of the patient to help retain the support member 202 in place within the body of the patient. The third arm member 204-3 is configured to be coupled to a third portion of the body of the patient to help retain the support member 102 in place within the body of the patient to help retain the support member 202 in place within the body of the patient. In some embodiments, the first arm member 204-1 and the second arm member 204-2 are passed from the medial superior portion of the obturator membrane of the obturator foramen 302. In other embodiments, the first arm member 204-1 and the second arm member 204-2 are passed through the inferior portion of the obturator membrane of the obturator foramen 302. This permits at least two arm members 204-1 and 204-2 to be brought up on each side of the obturator membrane. In some embodiments, the first arm member 204-1 and the second arm member 204-2 may each extend through an obturator and out a skin incision. Further, the third arm member 204-3 may be extended from the rectum 304 and attached to the coccyx 306. The flexibility in the length of the arm members 204 may allow the bodily implant 200 to be disposed around any size of the rectum 304 in the body of the patient.

The support member 202 is disposed such that it substantially surrounds the rectum 304 completely in the shape of an annular ring facilitating good contact with the anatomy to be supported. The curves of the support member 202 allow complementing the ano-rectal angle after the bodily implant 200 is placed around the rectum 304. In some embodiments, the support member 202 can be manually adjusted into the desired position in the body of the patient during placement. In some embodiments, the support member 202 constricts or kinks the rectum 304 by completely surrounding it.

Figure 4:
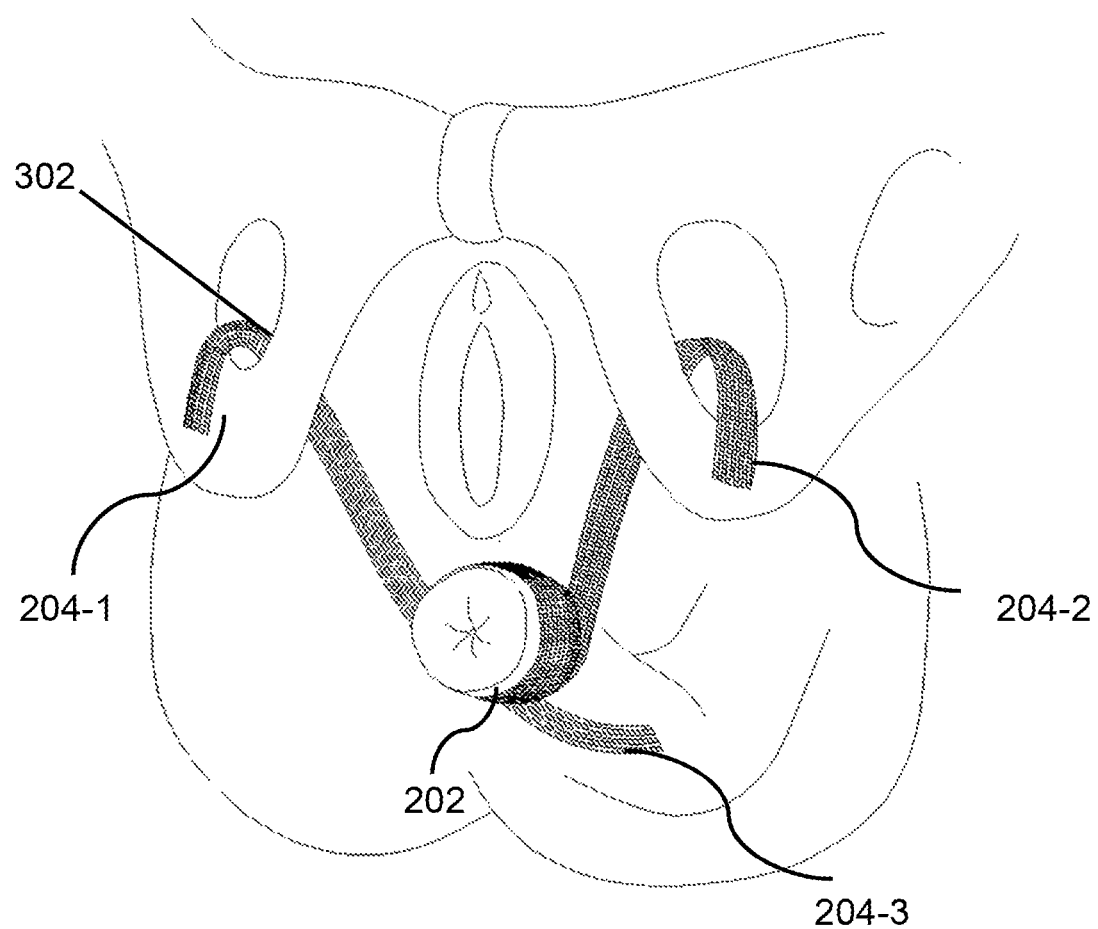
FIG. 4 schematically illustrates the bodily implant of FIG. 2 disposed within a pelvic region of a patient.

FIG. 4 schematically illustrates the bodily implant 200 disposed within the pelvic region of the patient. As shown in FIG. 4, the support member 202 completely surrounds the rectum 304.

Figure 5:
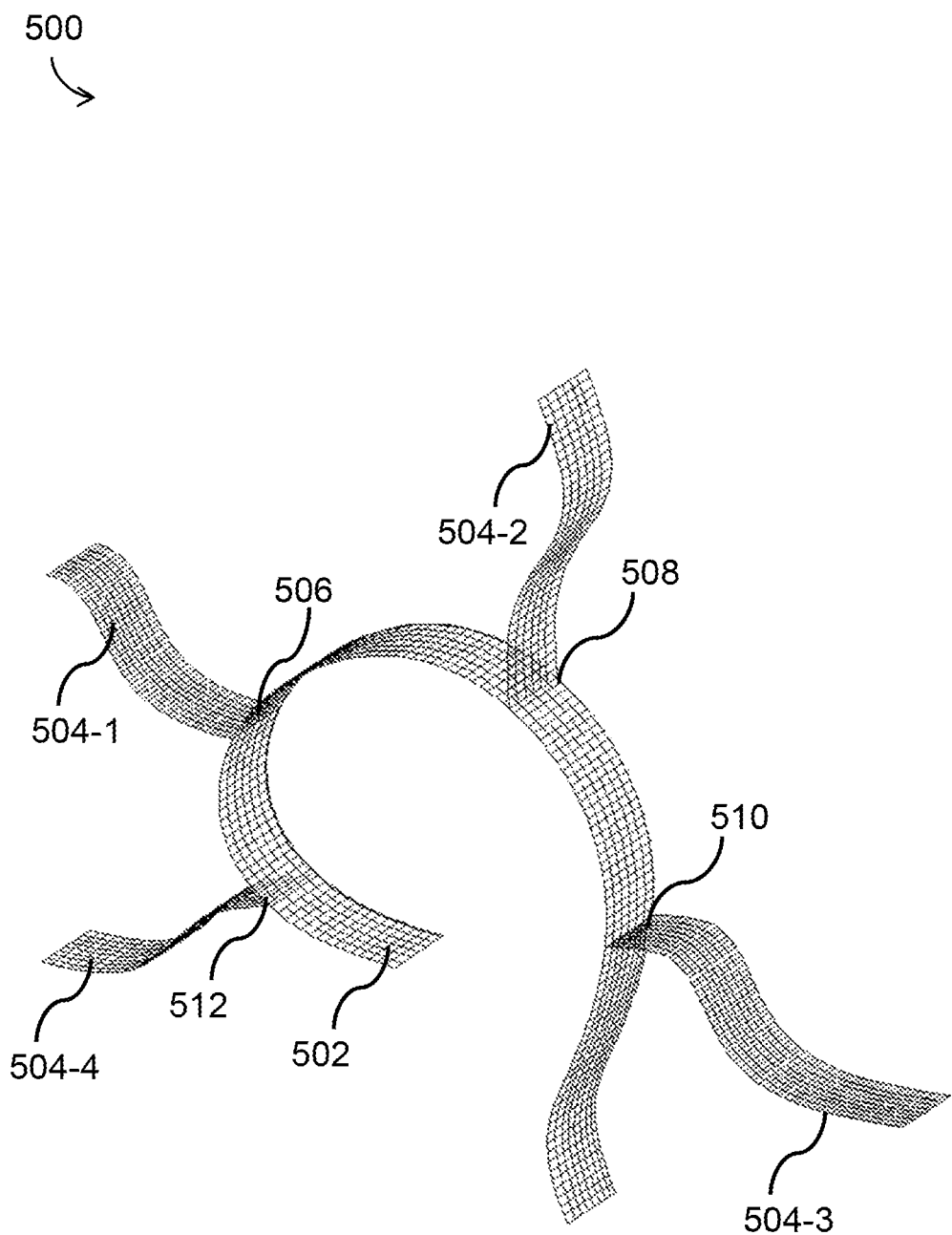
FIG. 5 is a schematic diagram of a bodily implant configured to be delivered into a patient's body for the treatment of fecal incontinence, in accordance with an embodiment of the present invention.

FIG. 5 is perspective view of a bodily implant 500 configured to be delivered into a patient's body for the treatment of fecal incontinence, in accordance with an embodiment of the present invention. The bodily implant 500 includes the support member 502 and four arm members 504-1, 504-2, 504-3, and 504-4, collectively referred to as 504. The structural and functional details of the support member 502 and the arm members 504 have been described in conjunction with FIG. 1 in detail. The four arm members 504 extend from four different locations 506, 508, 510, and 512 of the support member 502. Further, the support member 502, disposed between the four arm members 104, is structured in a manner such that it completely surrounds the rectum 304. A first arm member 504-1 extending from the support member 502 at a first location 506 is configured to be coupled to a first portion of the body of the patient to help retain the support member 502 in place within the body of the patient. A second arm member 504-2 extending from the support member 502 at a second location 508 is configured to be coupled to a second portion of the body of the patient to help retain the support member 502 in place within the body of the patient. A third arm member 504-3 extending from the support member 502 at a third location 510 is configured to be coupled to a third portion of the body of the patient to help retain the support member 502 in place within the body of the patient. A fourth arm member 504-4 extending from the support member 502 at a fourth location 512 is configured to be coupled to a fourth portion of the body of the patient to help retain the support member 502 in place within the body of the patient. In some embodiments, the support member 502 may also include a first coupling portion and a second coupling portion such that the first coupling portion is configured to be coupled to the second coupling portion. In such embodiments, support member 502 may be inserted into a body of a patient and the first coupling portion may be engaged and coupled to the second coupling portion such that the support member 502 forms a ring or loop around a rectum of the patient. The first and second coupling members could be portions of a snap or button type system.

The shape, size, and configuration of the bodily implant 500 may vary similar to the manner described in conjunction with FIG. 1 in detail.

Figure 6A:
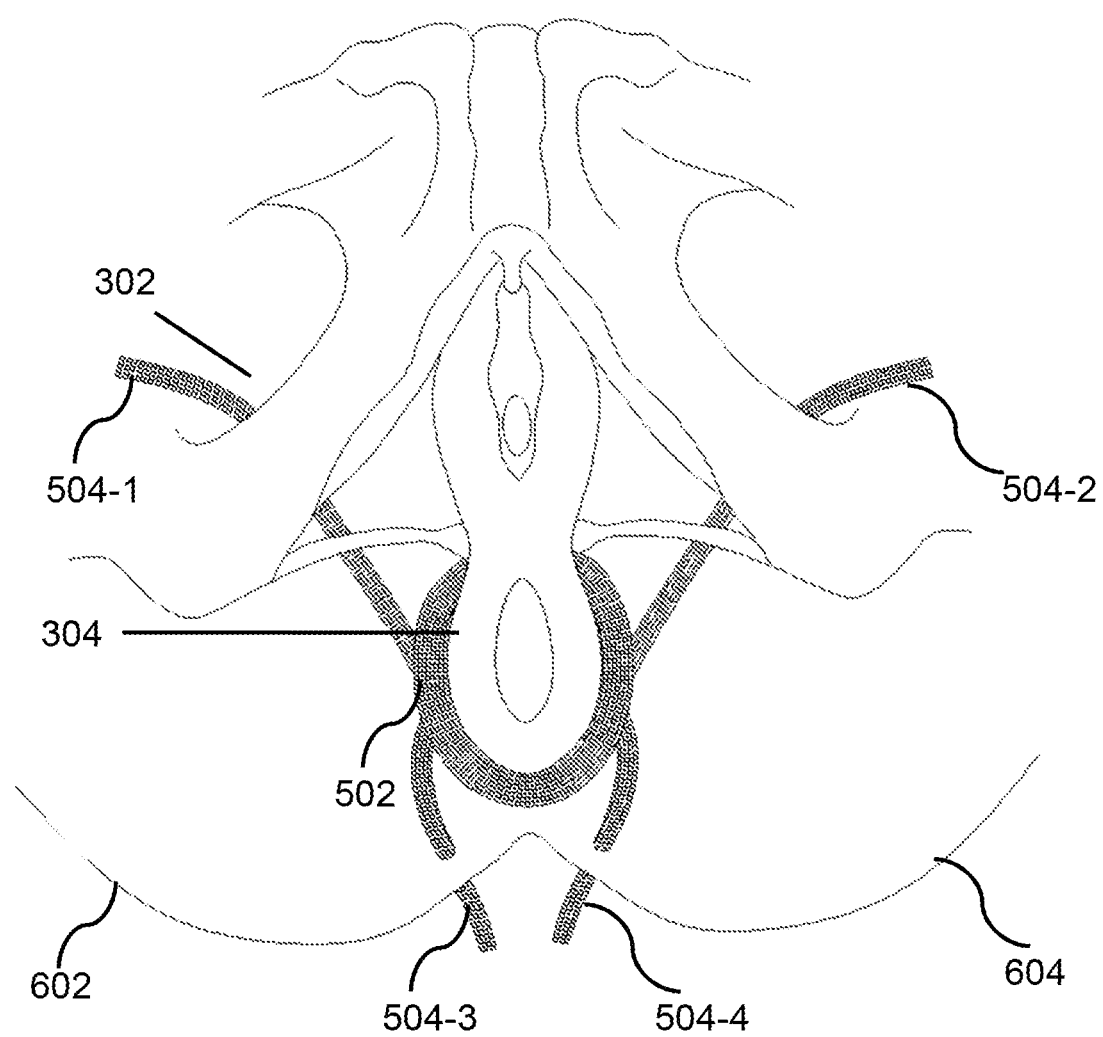
FIG. 6A schematically illustrates the bodily implant of FIG. 5 disposed within a patient's body, in accordance with an embodiment of the present invention.

FIG. 6A schematically illustrates the bodily implant 500 disposed within the patient's body, in accordance with an embodiment of the present invention. Referring to FIG. 6, the structure of the recto-genital region of a female patient is schematically depicted with the flexible support member 502 along with the four arm members 504 in place. In embodiments, the support member 502 is placed within the body tissues of the patient such that it completely surrounds the rectum 304 of the patient.

Figure 6B:
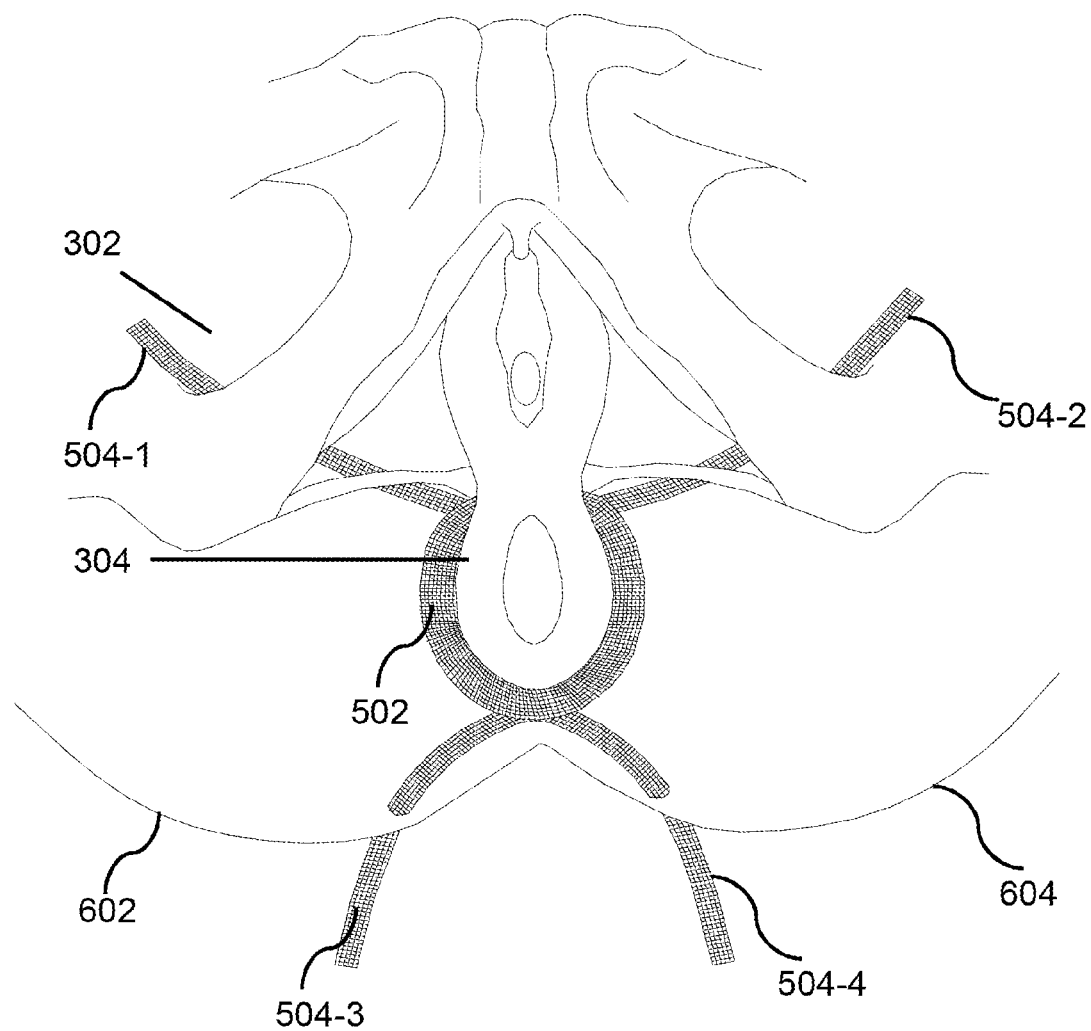
FIG. 6B schematically illustrates the bodily implant of FIG. 5 disposed within a patient's body, in accordance with an embodiment of the present invention.

In FIG. 6A the bodily implant 500 is disposed within the patient's body such that the arm members 504 extend from the support member 502 along the sides of the support (adjacent the sides of the patient's body). As illustrated in FIG. 6B, the bodily implant 500 may be disposed within the patient's body such that the arm members 504 extend from the support member 502 at the top and bottom of the support member.

In some embodiments, the four arm members 504 extend up through the medial portion of the obturator membrane of the obturator foramen 302. In an embodiment, the four arm members 504 may extend from a left pathway end lateral and posterior to the rectum 304 through the perineum (located between the anterior side of the anal sphincter and the posterior vaginal wall) and to a right pathway end in lateral (i.e., on the patient's right side) and posterior locations to the rectum 304.

In some embodiments, the first arm member 504-1 and the second arm member 504-2 are passed from the medial superior portion of the obturator membrane of the obturator foramen 302 on either side. In other embodiments, the first arm member 504-1 and the second arm member 504-2 are passed through the inferior portion of the obturator membrane of the obturator foramen 302. This permits two of the arm members 504 to be brought up on each side of the obturator membrane. The flexibility in the length of the arm members 104 allows the bodily implant 500 to be disposed around any size of the rectum 304 in the body of the patient.

In some embodiments, a first incision and a second incision may be made at the two buttocks 602 and 604, respectively, and approximately halfway between the body planar levels containing the rectum 304 and the coccyx 306 such as about 1.5 cm-2 cm lateral to the rectum 304. The third arm member 504-3 and the fourth arm member 504-4 may be pulled through the first incision and the second incision, and positioned so that the support member 502 rests around the rectum 304. In some embodiments, the third arm member 504-3 and the fourth arm member 504-4 may be fixed to any other anterior or posterior skin incisions, the coccyx bone, and the like. The arms can be sutured to skin proximate the incisions.

Therefore, in some embodiments, for placing the four arm members 104, two skin incisions are made at the obturator formaen 302 on each side and the two incisions are made at the left and the right buttocks 406 and 408, respectively. The skin incisions may be closed in a standard fashion with either sutures or glue.

In some embodiments, the first arm member 504-1 and the second arm member 504-2 are coupled to the upper side of the support member 502 on either side. In embodiments, the third arm member 504-3 and the fourth arm member 504-4 4 are coupled to the lower side of the support member 502 on either side. The support member 502 may be adjusted into the desired position in the body of the patient so that it constricts or kinks the rectum 304.

Figure 7A:
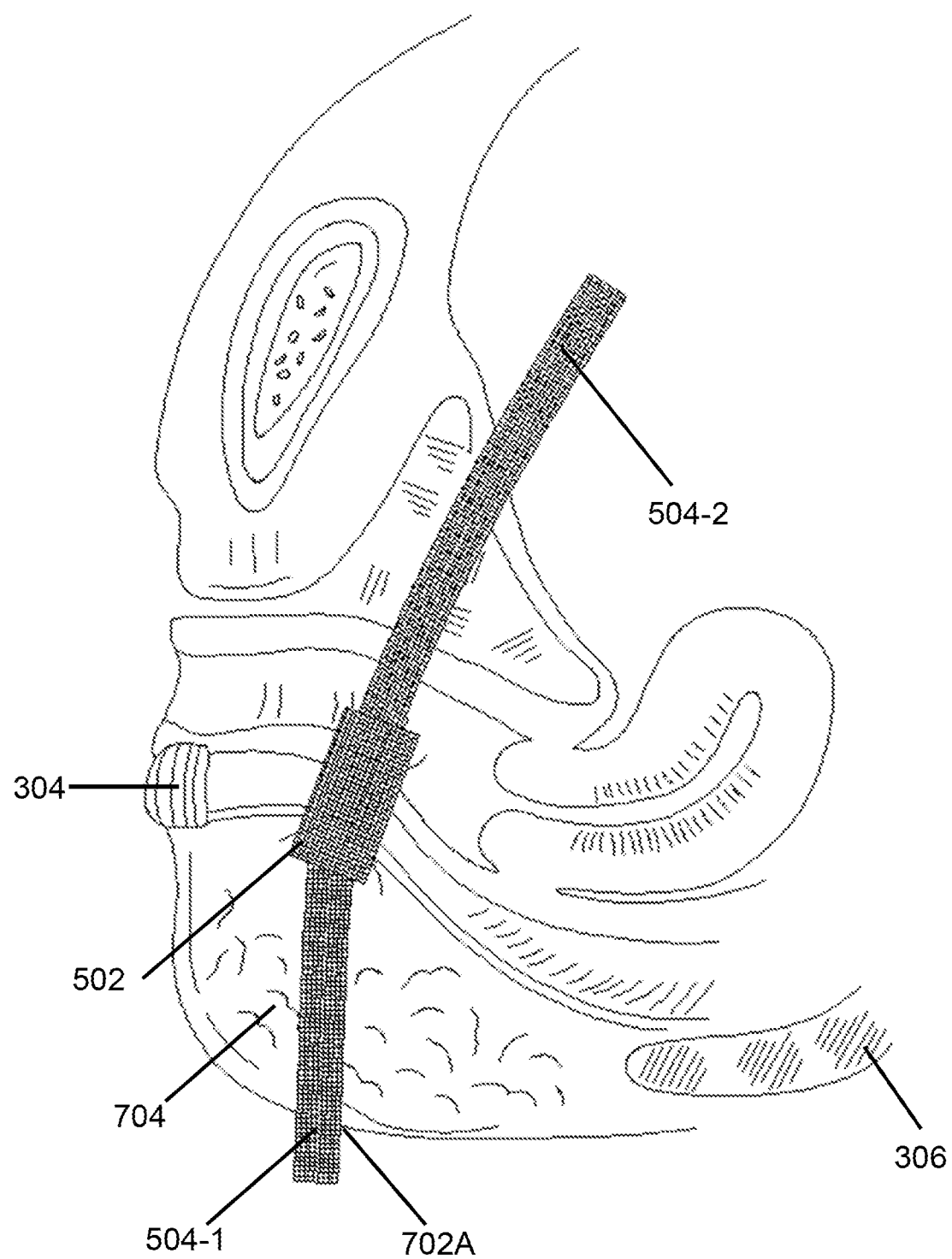
FIGS. 7A-7E schematically illustrate side views of bodily implants disposed within a patient's body in accordance with various embodiments of the present invention.
Figure 7B:
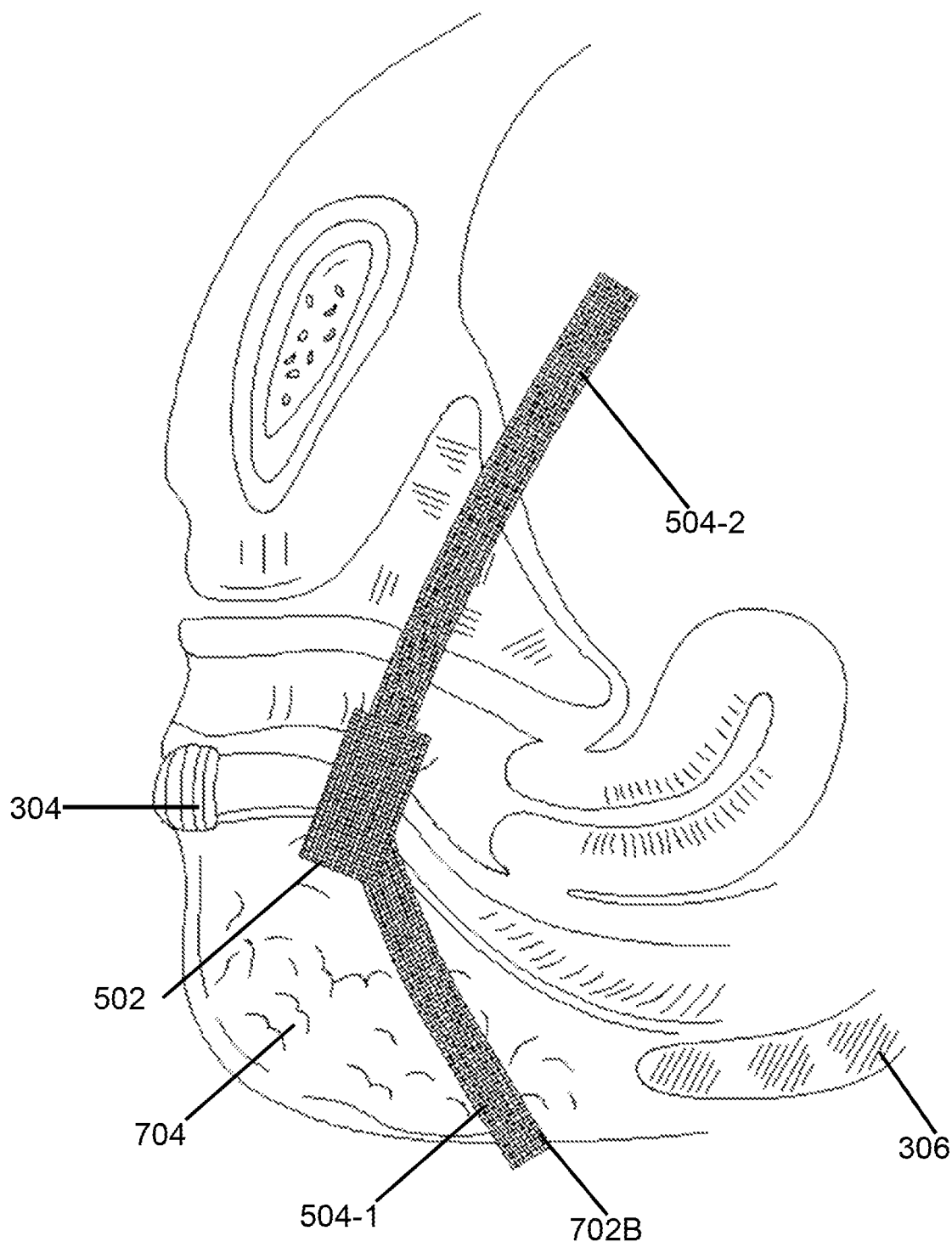
Figure 7C:
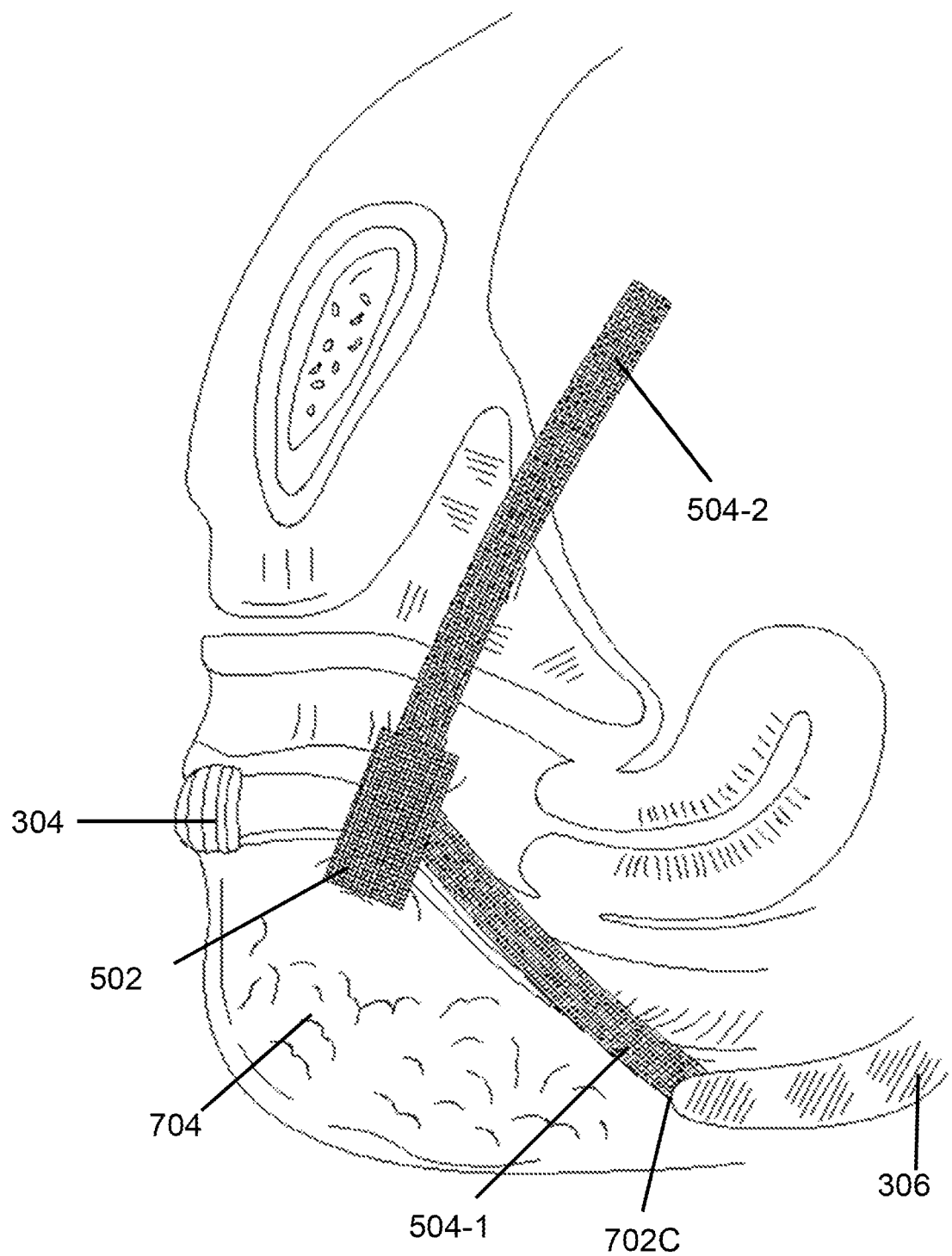
Figure 7D:
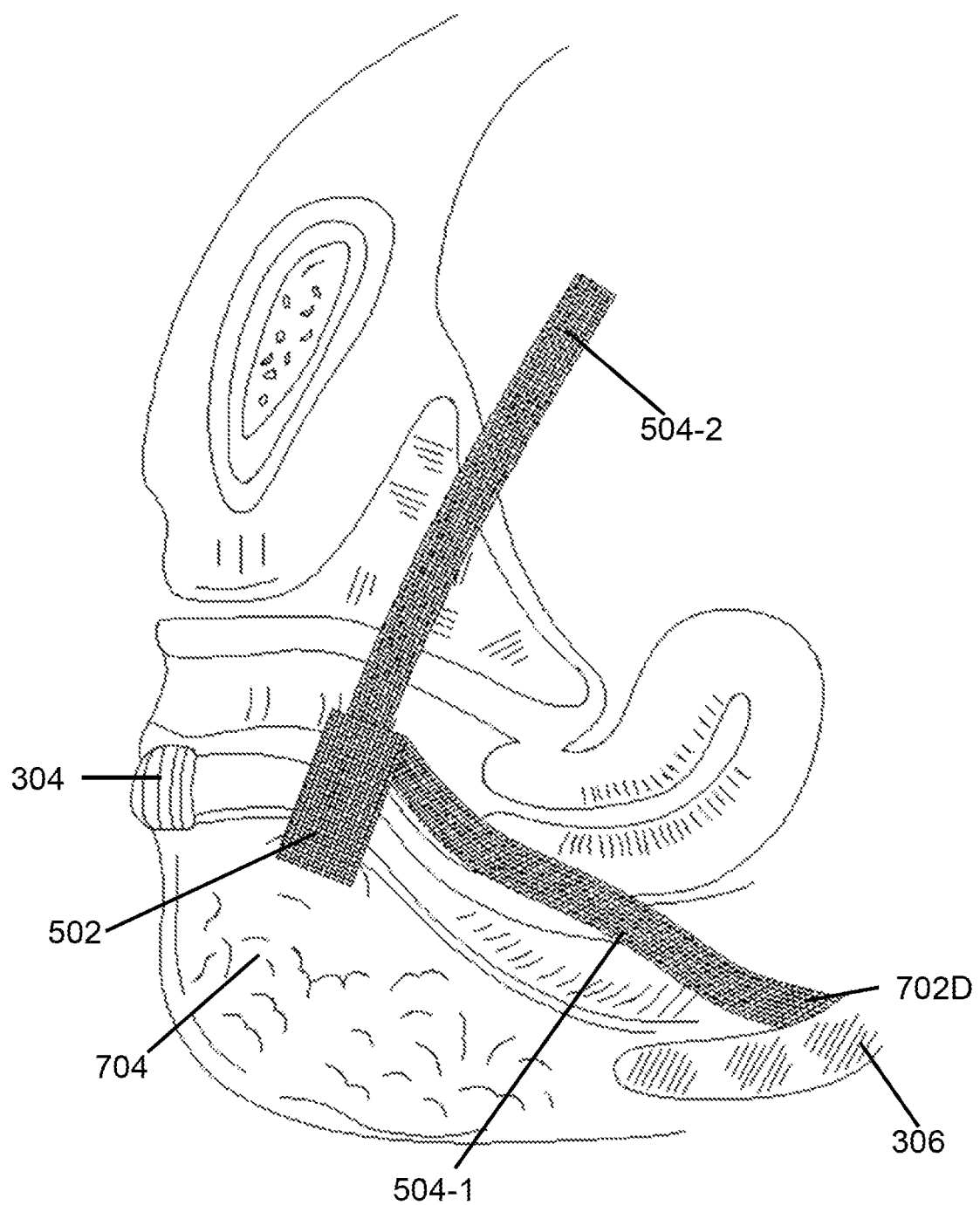

In some embodiments, the four arm members 504 (or the embodiments that include 3 arms) are configured to help retain the support member 502 such that a portion of the rectum 304 of the patient disposed on a first side of the support member 502 (i.e., the portion of the rectum below the support member 502) may form an angle with a portion of the rectum 304 of the patient disposed on a second side of the support member 502 (i.e., the portion of the rectum above the support member 502). This angle Ø is illustrated in FIG. 7D. In an embodiment, the four arm members 504 may be configured such that the portion of the rectum 304 of the patient disposed on a first side of the support member 502 (such as the portion of the rectum disposed between the implant and the anus) forms an acute angle with the portion of the rectum 304 of the patient disposed on a second side of the support member 502 (such as the portion of the rectum on the opposite side of the implant from the anus). In another embodiment, the four arm members 504 may be configured such that the portion of the rectum 304 of the patient disposed on the first side of the support member 502 forms an obtuse angle with the portion of the rectum 304 of the patient disposed on the second side of the support member 502. In some embodiments, the portion of the rectum 304 of the patient disposed on a first side of the support member 502 forms a right angle with the portion of the rectum 304 of the patient disposed on a second side of the support member 502. In some embodiments, the angle facilitates in keeping the feces in the rectum 304 until voluntary defecation.

In accordance with several embodiments, the ano-rectal angle may be evaluated for pre-operative diagnosis, intra-operative adjustment, and/or post-operative evaluation. The amount of flexion may be measured, thereby establishing the shape of the ano-rectal angle. Also, the ano-rectal angle formed before and after the placement of the bodily implant 500 may be measured. Subsequent to the measurement of the angle created by the rectum 304, the angle may also be communicated to a surgeon or medical practitioner for further treatment of the fecal incontinence.

FIGS. 7A-7E schematically illustrate side views of bodily implants such as the bodily implant 100, the bodily implant 200, and/or the body implant 500 disposed within a patient's body in accordance with various embodiments of the present invention. In an exemplary scenario, the invention is described in conjunction with the bodily implant 500 herein; however, the bodily implant 100 or 200 may also be employed.

Figure 7E:
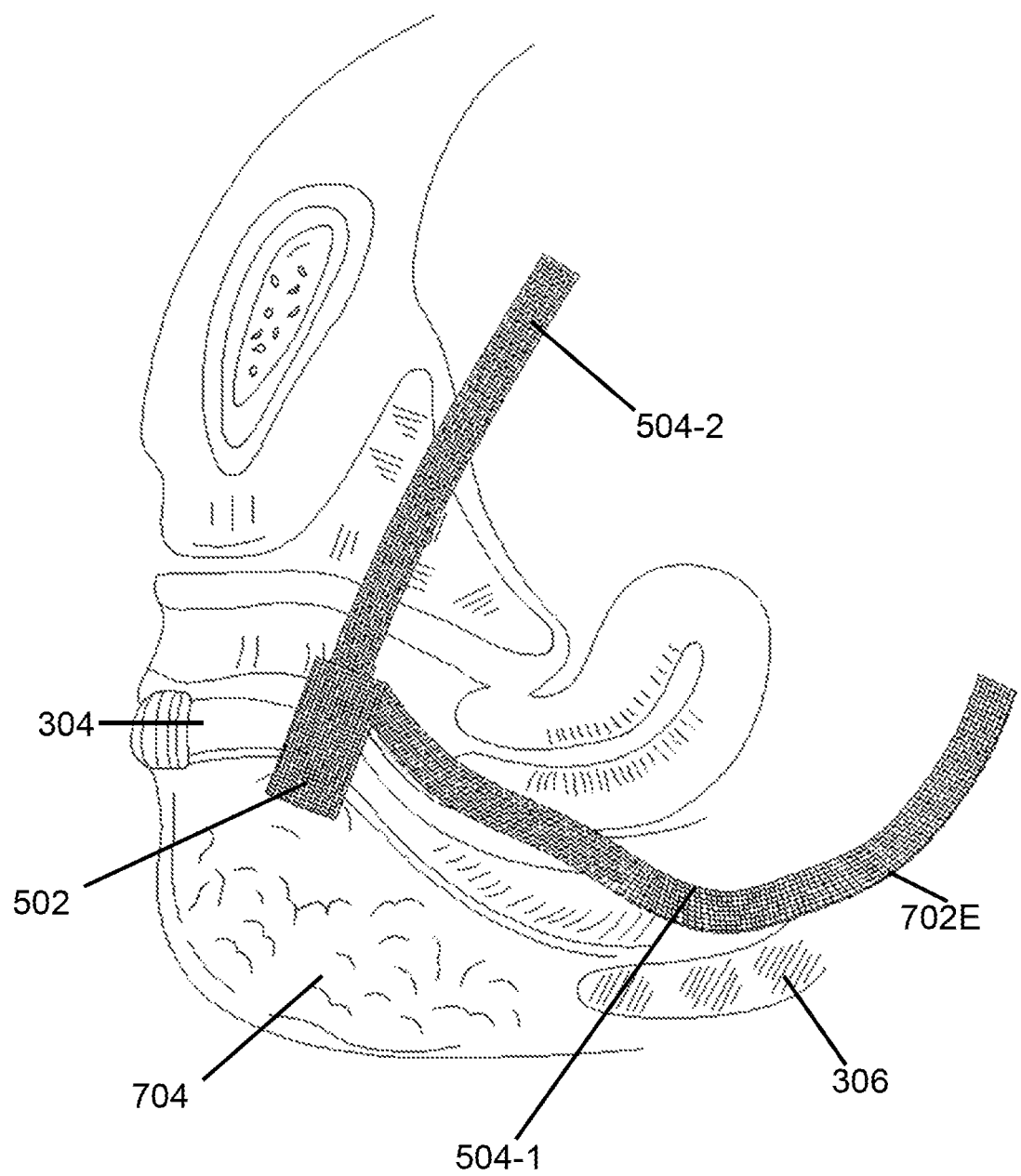

The optimal position of the bodily implant 500 within the patient's body may be determined based on the amount of tension required around the rectum 304. The amount of tension around the rectum 304 may be varied by alteration in the position of the four arm members 504 within the body of the patient. There can be various portions within the body of the patient where the four arm members 504 of the bodily implant 500 may be coupled or fixed to. As shown in FIG. 7A, the first arm member 504-1 is attached to a position 702A that may be proximate the ischiorectal fossa 704. Further, as shown in FIG. 7B, the first arm member 504-1 is attached to a position 702B that may be disposed away from the ischiorectal fossa 704. As illustrated in FIGS. 7C and 7D, the first arm member 504-1 is attached to the coccyx 306 at a position 702C and 702D, respectively. As shown in FIG. 7E, the first arm member 104-1 is attached to a position 702E by means of 'sacrocolpopexy' surgical fixation technique. Sacrocolpopexy is performed from the abdomen to support the vagina/rectum to the ligament on the spine by using the bodily implant 500. In some embodiments, the first arm member 504-1 is attached from an anterior or posterior portion of a vaginal wall to a ligament of lower back bone or lumbar vertebrae of the patient at the position 702E.

Figure 8:
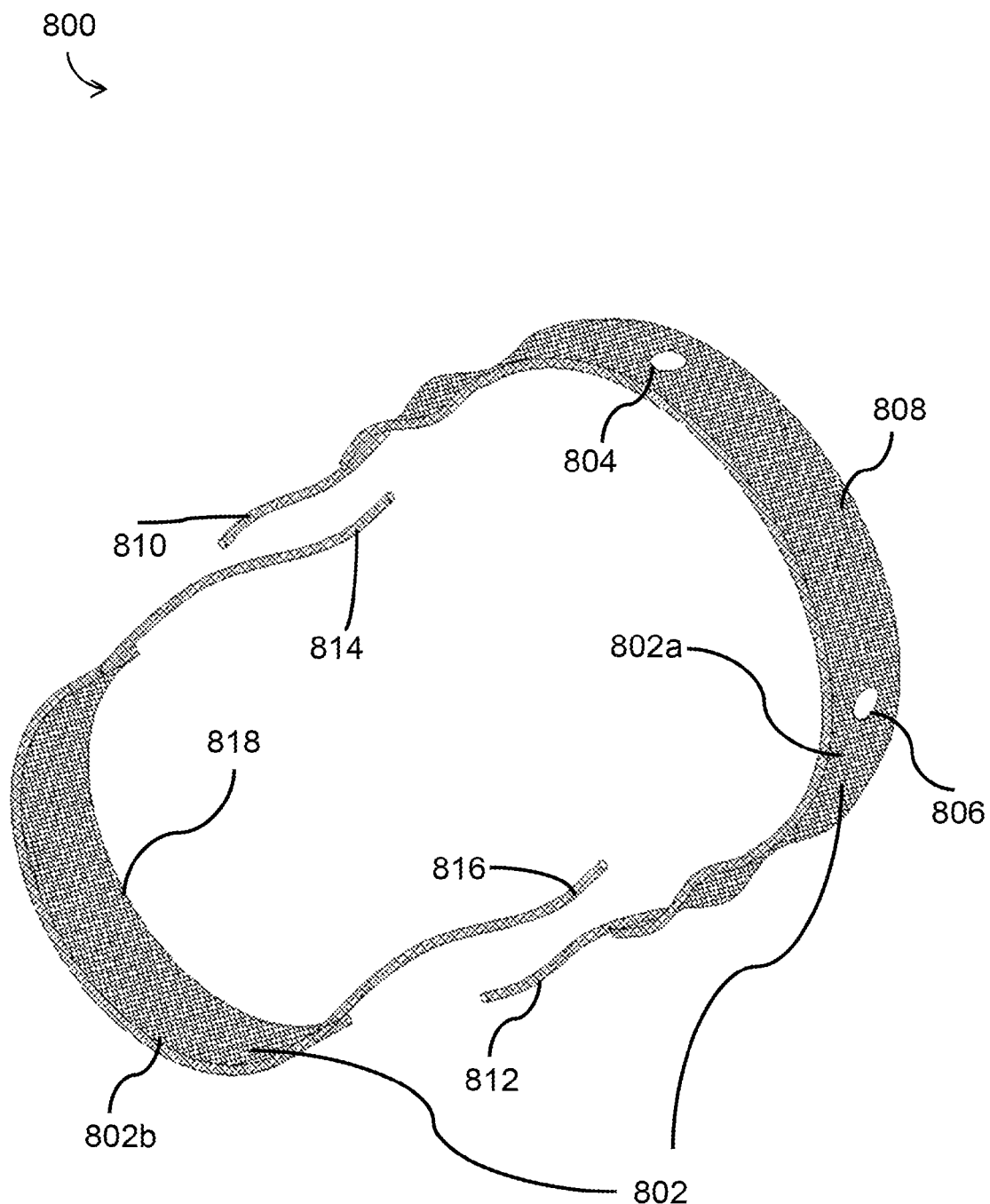
FIG. 8 is a perspective illustration of a bodily implant, in accordance with an embodiment of the present invention.
Figure 9:
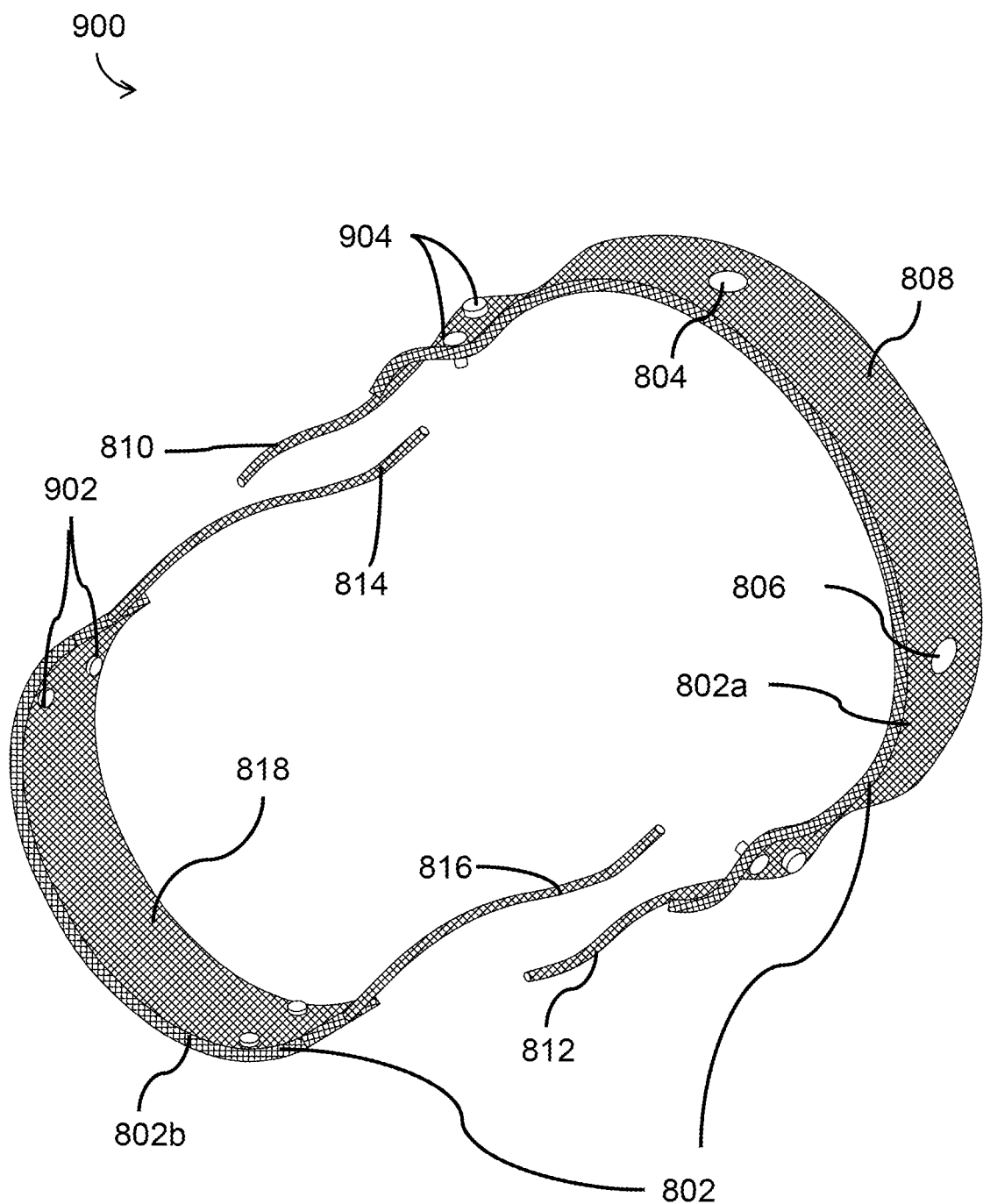
FIG. 9 is a perspective illustration of a bodily implant, in accordance with an embodiment of the present invention.

FIG. 8 is a perspective illustration of a bodily implant 800, in accordance with an embodiment of the present invention. The bodily implant 800 includes a support member 802. The support member 802 further includes a first member 802a and a second member 802b. In some embodiments, the first member 802a and the second member 802b are substantially linear. In other embodiments, various other shapes may also be possible. The first member 802a includes a first opening 804, a second opening 806, and a mid-portion 808 disposed between the first opening 804 and the second opening 806. The first member 802a further includes a first end portion 810 and a second end portion 812. The second member 802b includes a first end portion 814, a second end portion 816, and a mid-portion 818 disposed between the first end portion 814 and the second end portion 816. In some embodiments, the support member 802 may also include a first coupling portion 902 and a second coupling portion 904 as shown in FIG. 9 such that the first coupling portion 902 is configured to be coupled to the second coupling portion 904. The first and second coupling members 902 and 904 could be portions of a snap or button type system.

Figure 10A:
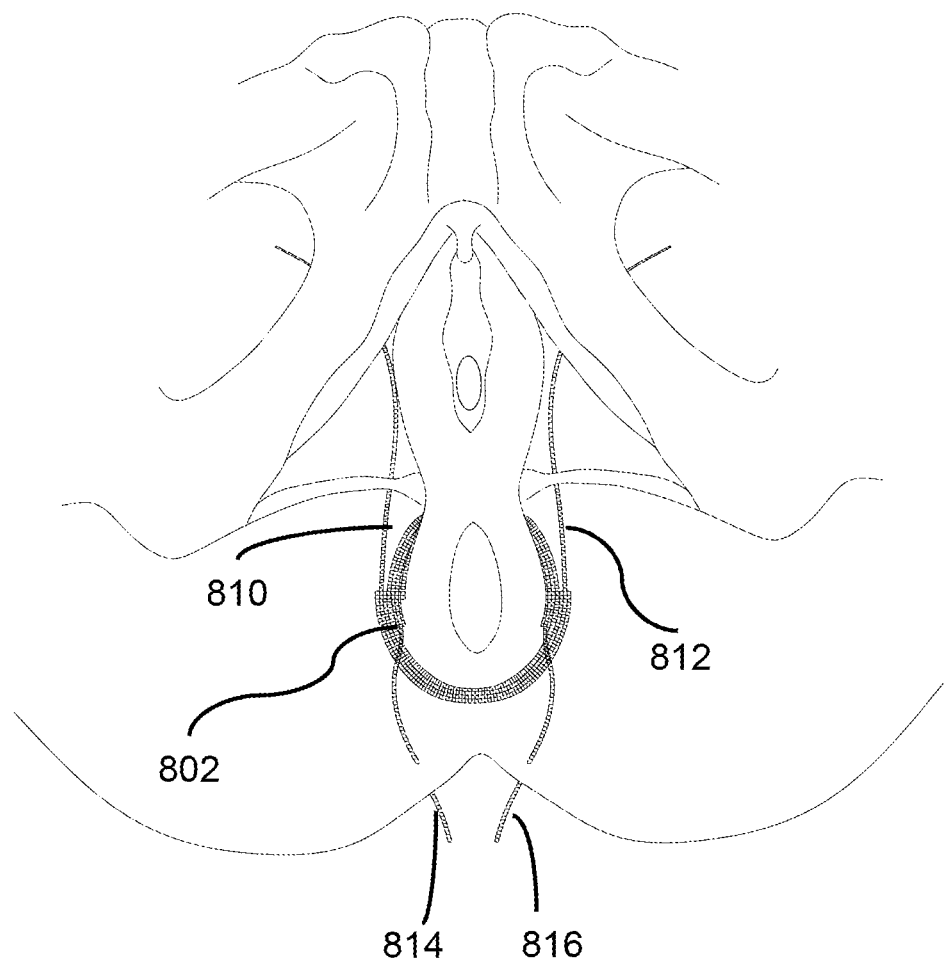
FIGS. 10A and 10B schematically illustrate front and side views of bodily implants respectively disposed within a patient's body in accordance with an embodiment of the present invention.
Figure 10B:
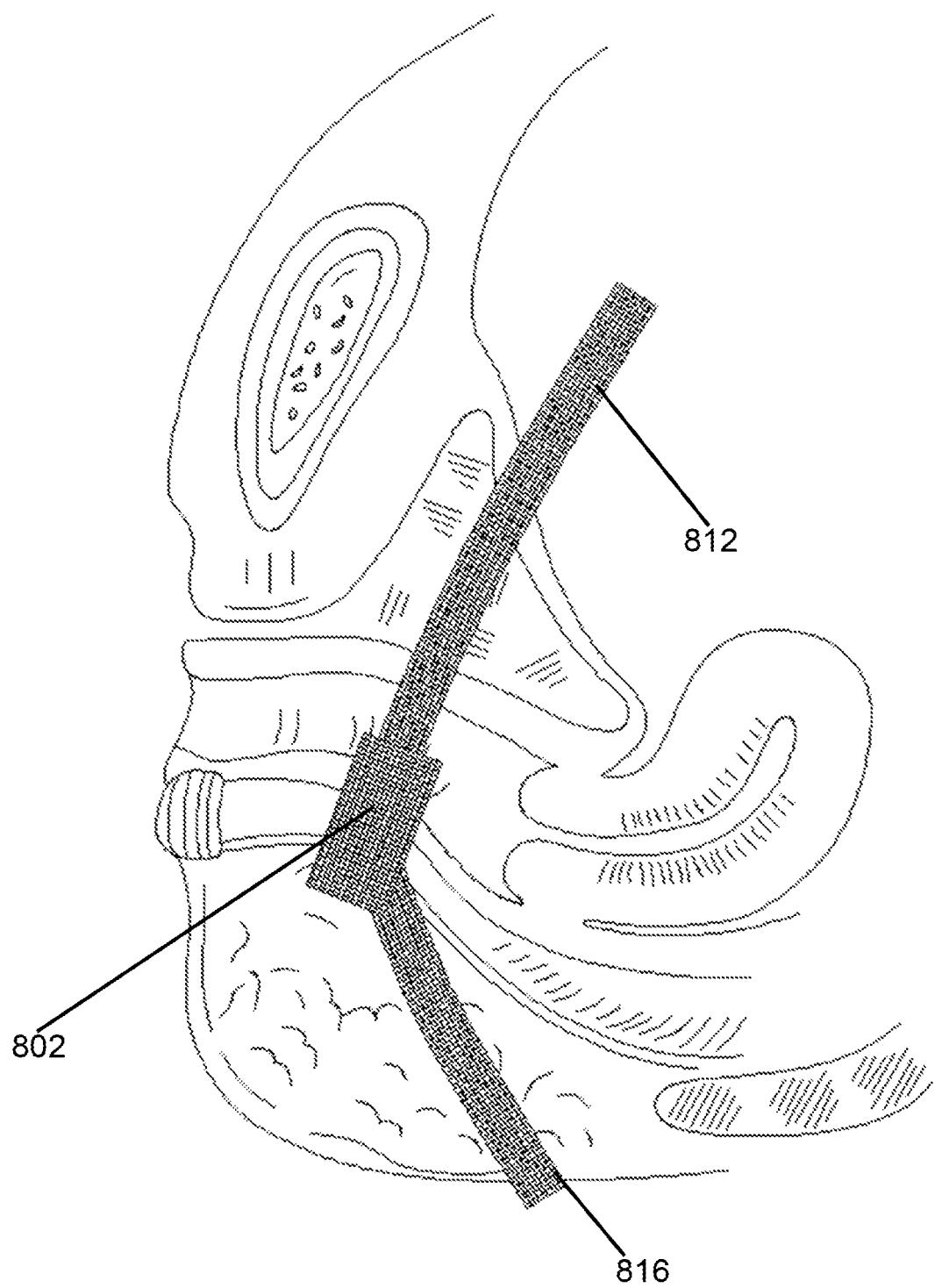

FIGS. 10A and 10B schematically illustrate front and side views of the bodily implant 800 respectively disposed within a patient's body in accordance with an embodiment of the present invention. In some embodiments, the second member 802b is configured to extend through the first opening 804 and the second opening 806 of the first member 802a. More particularly, the first member 802a is coupled to the second member 802b, such that the mid-portion 808 of the first member 802a and the mid-portion 818 of the second member 802b completely surrounds the rectum 304 of the patient, when disposed within the body of the patient.

The first end portion 814 of the second member 802b is configured to pass through the first opening 804 of the first member 802a upon placement inside the body. Similarly, the second end portion 816 of the second member 802b is configured to pass through the second opening 806 of the first member 802a. In an embodiment, the first end portion 814 and the second end portion 816 of the second member 802b may be removably coupled to the second member 802b. In another embodiment, the first end portion 814 and the second end portion 816 of the second member 802b may form an integral part of the second member 802b. Similarly, in an embodiment the first end portion 810 and the second end portion 812 of the first member 802a may be removably coupled to the first member 802a. In another embodiment, the first end portion 810 and the second end portion 812 of the first member 802a may form an integral part of the first member 802a.

In embodiments, the first member 802a is wrapped around a first portion of the rectum 304 of the patient. And, the second member 802b is wrapped around a second portion of the rectum 304 of the patient. Subsequently, the first member 802a is coupled to the second member 802b.

The first end portion 814 of the second member 802b is configured to be coupled to a first portion of the body of the patient to help retain the bodily implant 800 in place within the body of the patient. The second end portion 816 is configured to be coupled to a second portion of the body of the patient to help retain the bodily implant 800 in place within the body of the patient. In one embodiment, the first portion of the body of the patient may be located posterior to the rectum 304 of the patient. In another embodiment, the second portion of the body of the patient is located anterior to the rectum 304 of the patient. There can be various portions within the body of the patient where the end portions 810 and 812 of the first member 802a and the end portions 814 and 816 of the second member 802b of the bodily implant 800 may be coupled. In some embodiments, the end portions are attached to a position that may be proximate the ischiorectal fossa. In other embodiments, the end portions are attached to a position that may be disposed away from the ischiorectal fossa. In still other embodiments, the end portions may be attached to the coccyx. In some embodiments, the end portions are configured to pass through an obturator foramen or extend to the retropubic or suprapubic region of the patient.

Figure 11:
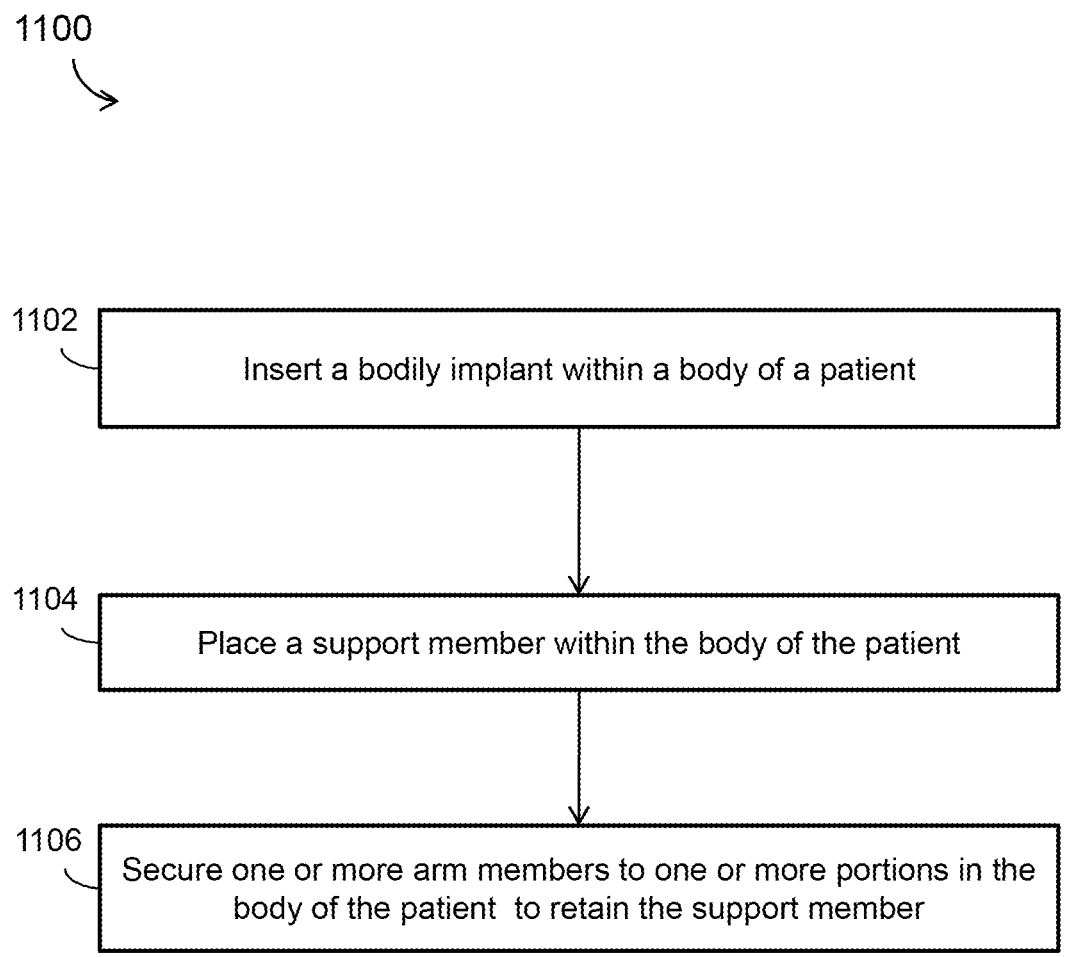
FIG. 11 is a flowchart illustrating a method of delivery and placement of a bodily implant, in accordance with various embodiments of the present invention.

FIG. 11 is a flowchart illustrating a method 1100 of delivery and placement of a bodily implant such as the bodily implant 100, the bodily implant 200, the bodily implant 500, and the bodily implant 800, in accordance with various embodiments of the present invention. As illustrated in FIG. 11, the method 1100 includes inserting the bodily implant (such as the bodily implant 100, 200, 500, and 800) within the body of the patient by making a bodily incision at step 1102. In some embodiments, the bodily incision is a vaginal incision. In other embodiments, the bodily incision is a buttock incision made on a right buttock and/or a left buttock. In still other embodiments, the bodily incision is a perennial incision made in the perennial body. Similarly, the bodily incision can be made at various possible locations for facilitating the insertion of the bodily implant (100, 200, 500, and 800) within the patient's body.

The method further includes placing a support member within the body of the patient at step 1104 such that the support member surrounds the rectum 304 of the patient.

In embodiments, the support member may be the support member 102, the support member 202, the support member 502 or the support member 802, which may be placed to completely surround the rectum 304. The support member (102, 202, 502, or 802) is disposed such that it substantially surrounds the rectum 304 completely in the shape of an annular ring facilitating good contact with the anatomy to be supported.

Now with further reference to FIG. 8, in some embodiments, the placing of the support member 802 further includes coupling a first portion of the support member 802 to a second portion of the support member 802. Also, in some embodiments, the placing may include wrapping the first portion of the support member 802 about a first portion of the rectum 304 of the patient, wrapping the second portion of the support member 802 to the second portion of the rectum 304, and coupling the first portion of the support member 802 to the second portion of the support member 802. In some embodiments, the first portion of the support member 802 is stitched or glued or otherwise coupled to the second portion of the support member 802 to form a loop or ring around the rectum. In other embodiments, the first portion of the support member 802 includes a first coupling member and the second portion of the support member 802 includes a second coupling member (as shown in FIG. 10) that is configured to be coupled to the first coupling member. For example, the first and second coupling members could be portions of a snap or button type system.

The method further includes securing one or more arm members at step 1006. In some embodiments, the one or more arm members extends from the support member (102, 202, 502, or 802) to a portion of the body of the patient to help retain the bodily implant (100, 200, 500, and 800) in place within the body of the patient.

In an embodiment, the one or more arm members may be similar to the three arm members 204-1, 204-2, and 204-3, collectively referred to as 204, as illustrated in conjunction with FIG. 2. Referring further to FIG. 2, the first arm member 204-1 extending from the support member 202 at the first location 206 is configured to be secured to the first portion of the body of the patient. The second arm member 204-2 extending from the support member 202 at the second location 208 is configured to be secured to the second portion of the body of the patient. The third arm member 204-3 extending from the support member 202 at the third location 210 is configured to be secured to the third portion of the body of the patient. The first arm member 204-1, the second arm member 204-2, and the third arm member 204-3 are secured to retain the support member 102 in place within the body of the patient. The three different locations 206, 208, and 210 for coupling the three arm members 204 on the support member 202 are spaced apart by a fixed distance. The fixed distance between the three different locations 206, 208, and 210 may be altered in accordance with various embodiments of the bodily implant 200 and based on the intended site of implantation.

There can be various portions within the body of the patient where the arm members 204 may be coupled. In some embodiments, the arm members 204 are attached to a position that may be proximate the ischiorectal fossa. In other embodiments, the arm members 204 are attached to a position that may be disposed away from the ischiorectal fossa. In still other embodiments, the arm members 204 may be attached to the coccyx. In some embodiments, the arm members 204 are configured to pass through an obturator foramen or extend to the retropubic or suprapubic region of the patient. In some embodiments, the arm members 204 are passed from the medial superior portion of the obturator membrane of the obturator foramen. In other embodiments, the arm members 204 are passed through the inferior portion of the obturator membrane of the obturator foramen. In some embodiments, the arm members 204 may extend through an obturator and out a skin incision. Further, the arm members may be extended from the rectum and attached to the coccyx.

In another embodiment, the one or more arm members may be similar to the four arm members 504-1, 504-2, 504-3, and 504-4, collectively referred to as 504, as illustrated in conjunction with FIG. 5. Referring further to FIG. 5, the four arm members 504 are secured to extend from four different locations 506, 508, 510, and 512 of the support member 502. The first arm member 504-1 extending from the support member 502 at the first location 506 is configured to be secured to the first portion of the body of the patient. The second arm member 504-2 extending from the support member 502 at the second location 508 is configured to be secured to the second portion of the body of the patient. The third arm member 504-3 extending from the support member 502 at the third location 510 is configured to be secured to the third portion of the body of the patient. The fourth arm member 504-4 extending from the support member 502 at the fourth location 512 is configured to be secured to the fourth portion of the body of the patient. The first arm member 504-1, the second arm member 504-2, the third arm member 504-3, and the fourth arm member 504-4 are secured to retain the support member 502 in place within the body of the patient. The four arm members 504 extending from the support member 504 and secured to four different portions or tissues in the body of the patient distribute the abdominal forces over a wide area in the body of the patient.

There can be various portions within the body of the patient where the arm members 504 may be coupled. In some embodiments, the arm members 504 are attached to a position that may be proximate the ischiorectal fossa. In other embodiments, the arm members 504 are attached to a position that may be disposed away from the ischiorectal fossa. In still other embodiments, the arm members 504 may be attached to the coccyx. In some embodiments, the arm members 504 are configured to pass through an obturator foramen or extend to the retropubic or suprapubic region of the patient. In some embodiments, the arm members 504 are passed from the medial superior portion of the obturator membrane of the obturator foramen. In other embodiments, the arm members 504 are passed through the inferior portion of the obturator membrane of the obturator foramen. In some embodiments, the arm members 504 may extend through an obturator and out a skin incision. Further, the arm members 504 may be extended from the rectum and attached to the coccyx.

In still another embodiment, the one or more arm members may be similar to the first end portion 810, the second end portion 812 of the first member 802a, and the first end portion 814, and the second end portion 816 of the second member 802b, as illustrated in FIG. 8. Referring further to FIG. 8, the first end portion 814 of the second member 802b is configured to be secured to a first portion of the body of the patient to help retain the bodily implant 800 in place within the body of the patient. The second end portion 816 is configured to be secured to a second portion of the body of the patient to help retain the bodily implant 800 in place within the body of the patient. In one embodiment, the first portion of the body of the patient may be located posterior to the rectum 304 of the patient and the second portion of the body of the patient is located anterior to the rectum 304 of the patient. The arm members are secured to the body tissues such that a kink is formed around the rectum 304 of the patient.

There can be various portions within the body of the patient where the end portions 810 and 812 of the first member 802a and the end portions 814 and 816 of the second member 802b may be coupled. In some embodiments, the end portions 810 and 812 of the first member 802a and the end portions 814 and 816 of the second member 802b are attached to a position that may be proximate the ischiorectal fossa. In other embodiments, the end portions 810 and 812 of the first member 802a and the end portions 814 and 816 of the second member 802b are attached to a position that may be disposed away from the ischiorectal fossa. In still other embodiments, the end portions 810 and 812 of the first member 802a and the end portions 814 and 816 of the second member 802b may be attached to the coccyx. In some embodiments, the end portions 810 and 812 of the first member 802a and the end portions 814 and 816 of the second member 802b are configured to pass through an obturator foramen or extend to the retropubic or suprapubic region of the patient. In some embodiments, the end portions 810 and 812 of the first member 802a and the end portions 814 and 816 of the second member 802b are passed from the medial superior portion of the obturator membrane of the obturator foramen. In other embodiments, the end portions 810 and 812 of the first member 802*a* and the end portions 814 and 816 of the second member 802*b* are passed through the inferior portion of the obturator membrane of the obturator foramen. In some embodiments, the end portions 810 and 812 of the first member 802*a* and the end portions 814 and 816 of the second member 802*b* may extend through an obturator and out a skin incision. Further, the end portions 810 and 812 of the first member 802*a* and the end portions 814 and 816 of the second member 802*b* may be extended from the rectum and attached to the coccyx.

In some embodiments, the bodily implants as described in accordance with various embodiments, may be tied with for example sutures, staples, adhesives, pins, and the like. In other embodiments, the pressure from the body tissues may provide enough support for fixing the bodily implants with the body tissues.

In some embodiments, a bodily implant includes a support member configured to be placed within a body of a patient such that the support member surrounds at least a portion of a rectum of the patient and an arm member extending from the support member and configured to be coupled to a portion of the body of the patient to help retain the support member in place within the body of the patient.

In some embodiments, the support member is composed of a flexible material. In some embodiments, the arm member includes an elastic material. In some embodiments, the arm member extends from the support member to a location posterior to an anus of the patient. In some embodiments, the arm member extends from the support member to a location anterior to an anus of the patient.

In some embodiments, the arm member is a first arm member, the portion of the body of the patient is a first portion of the body of the patient, and the bodily implant further includes a second arm member extending from the support member and configured to be coupled to a second portion of the body of the patient to help retain the support member in place within the body of the patient, and a third arm member extending from the support member and configured to be coupled to a third portion of the body of the patient to help retain the support member in place within the body of the patient.

In some embodiments, the arm member is a first arm member, the portion of the body of the patient is a first portion of the body of the patient, the bodily implant further includes a second arm member extending from the support member and configured to be coupled to a second portion of the body of the patient to help retain the support member in place within the body of the patient, the second portion of the body of the patient being located posteriorly to an anus of the patient, and a third arm member extending from the support member and configured to be coupled to a third portion of the body of the patient to help retain the support member in place within the body of the patient, the third portion of the body of the patient being located anteriorly to the anus of the patient.

In some embodiments, the arm member is a first arm member, the portion of the body of the patient is a first portion of the body of the patient, the bodily implant further includes a second arm member extending from the support member and configured to be coupled to a second portion of the body of the patient to help retain the support member in place within the body of the patient, a third arm member extending from the support member and configured to be coupled to a third portion of the body of the patient to help retain the support member in place within the body of the patient, and a fourth arm member extending from the support member and configured to be coupled to a fourth portion of the body of the patient to help retain the support member in place within the body of the patient.

In some embodiments, the arm member is configured to help retain the support member within the body of the patient such that an angle is formed by the rectum. In some embodiments, the arm member is configured to help retain the support member within the body of the patient such that a portion of the rectum of the patient disposed on a first side of the support member forms an angle with a portion of the rectum of the patient disposed on a second side of the support member.

In some embodiments, the arm member is configured to help retain the support member within the body of the patient such that a portion of the rectum of the patient disposed on a first side of the support member forms an acute angle with a portion of the rectum of the patient disposed on a second side of the support member.

In some embodiments, the support member includes a first coupling portion and a second coupling portion. The first coupling portion is configured to be coupled to the second coupling portion to form a ring around the rectum in the body of the patient.

In some embodiments, a bodily implant includes a first member defining a first opening and a second opening and having a mid-portion disposed between the first opening and the second opening, and a second member having a first end portion, a second end portion and a mid-portion disposed between the first end portion and the second end portion. The second member is configured to extend though the first opening and the second opening. The first member and the second member are configured to be disposed within a body of a patient such that the mid-portion of the first member and the mid-portion of the second member surround a rectum of the patient. The first end portion of the second member is configured to be coupled to a portion of the body of the patient to help retain the bodily implant in place within the body of the patient.

In some embodiments, the first member and the second member are substantially semi-circular in shape when disposed within the body of the patient. In some embodiments, the first member and the second member are composed of a flexible material. In some embodiments, the portion of the body of the patient is located anteriorly to the anus of the patient. In some embodiments, the portion of the body of the patient is located posteriorly to the anus of the patient. In some embodiments, the portion of the body of the patient is a first portion of the body of the patient, wherein the first member includes an end portion configured to be coupled to a second portion of the body of the patient to help retain the bodily implant in place within the body of the patient.

In some embodiments, the portion of the body of the patient is a first portion of the body of the patient, wherein the first member includes an end portion configured to be coupled to a second portion of the body of the patient to help retain the bodily implant in place within the body of the patient. The first portion of the body of the patient is located posteriorly of an anus of the patient. The second portion of the body of the patient is located anteriorly of the anus of the patient.

In some embodiments, a method for placement of a bodily implant within a body of a patient includes (1) placing a support member within the body of the patient such that the support member surrounds a rectum of a patient; and (2) securing an arm member that extends from the support member to a portion of the body of the patient to help retain the bodily implant in place within the body of the patient.

In some embodiments, the placing includes coupling a first portion of the support member to a second portion of the support member. In some embodiments, the placing includes wrapping a first portion of the support member about a first portion of the rectum of the patient, wrapping a second portion of the support member about a second portion of the rectum, and coupling the first portion of the support member to the second portion of the support member. In some embodiments, the securing includes securing the arm member to a portion of the body of the patient that is located anteriorly to an anus of the patient. In some embodiments, the securing includes securing the arm member to a portion of the body of the patient that is located posteriorly to an anus of the patient.

In some embodiments, the method includes forming a kink in the rectum of the patient.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

What is claimed is:

1. A bodily implant comprising:
a support member configured to be placed within a body of a patient, the support member being configured to fully surround at least a portion of a rectum of the patient such that the support member forms a loop around the portion of the rectum, the support member including a first end having a first coupling portion, the support member including a second end having a second coupling portion, the support member having a first lateral edge and a second lateral edge, the first and second lateral edges extending from the first end to the second end, the first and second lateral edges being parallel to a longitudinal axis of the support member; and
a mesh arm member extending from the support member and configured to be coupled to a portion of the body of the patient to help retain the support member in place within the body of the patient,
the support member including an inner surface and an outer surface opposite to the inner surface, the inner surface configured to engage the portion of the rectum when the support member forms the loop around the portion of the rectum,
the mesh arm member being coupled to a portion of the outer surface between the first end and the second end of the support member, the mesh arm member extending from the first lateral edge to the second lateral edge along an axis perpendicular to the longitudinal axis,
the first coupling portion of the support member configured to be coupled to the second coupling portion of the support member,
wherein the support member is configured to form the loop by coupling the first coupling portion and the second coupling portion.

2. The bodily implant of claim 1, wherein the loop formed around the portion of the rectum is a complete loop.

3. The bodily implant of claim 1, wherein the mesh arm member and the support member include an elastic material.

4. The bodily implant of claim 1, wherein the mesh arm member is of a length capable of extending from the support member to a location posterior to an anus of the patient.

5. The bodily implant of claim 1, wherein the mesh arm member is of a length capable of extending from the support member to a location anterior to an anus of the patient.

6. The bodily implant of claim 1, wherein the mesh arm member is a first arm member extending from a first location on the outer surface of the support member, the portion of the body of the patient being a first portion of the body of the patient, the bodily implant further comprising:
a second arm member extending from a second location on the outer surface of the support member and configured to be coupled to a second portion of the body of the patient to help retain the support member in place within the body of the patient; and
a third arm member extending from a third location on the outer surface of the support member and configured to be coupled to a third portion of the body of the patient to help retain the support member in place within the body of the patient,
wherein the first location, the second location, and the third location are linearly disposed along the longitudinal axis of the support member.

7. The bodily implant of claim 6, the bodily implant further comprising:
a fourth arm member extending from a fourth location on the outer surface of the support member and configured to be coupled to a fourth portion of the body of the patient to help retain the support member in place within the body of the patient,
wherein the first location, the second location, the third location, and the fourth location are linearly disposed along the longitudinal axis of the support member.

8. The bodily implant of claim 1, wherein a distance between the outer surface of the support member and the inner surface of the support member defines a thickness of the support member.

9. The bodily implant of claim 1, the bodily implant further comprising:
a plurality of mesh arm members including the mesh arm member, the plurality of mesh arm members being coupled to the outer surface of the support member at different locations along the longitudinal axis of the support member, each mesh arm member extending from the first lateral edge to the second lateral edge, wherein the plurality of mesh arm members are equally spaced along the longitudinal axis of the support member.

10. The bodily implant of claim 9, wherein the portion of the outer surface coupled to the mesh arm member is disposed in a plane, the mesh arm member extending in a direction orthogonal to the plane.

11. A bodily implant comprising:
a first support member defining a first opening and a second opening, the first support member having a portion disposed between the first opening and the second opening; and
a second support member having a first terminal end portion, a second end terminal portion, and a portion disposed between the first terminal end portion and the second terminal end portion of the second support member, the second support member having a first extension member extending from the first terminal end portion of the second support member and a second extension member extending from the second terminal end portion of the second support member,
the first extension member of the second support member being configured to extend through the first opening of the first support member, the second extension member being configured to extend through the second opening of the first support member such that the portion disposed between the first opening and the second opening of the first support member and the portion disposed between the first terminal end portion and the second terminal end portion of the second support member are configured to form a loop around a portion of a rectum of a patient.

12. The bodily implant of claim 11, wherein the first support member and the second support member are substantially semi-circular in shape when disposed within a body of the patient.

13. The bodily implant of claim 11, wherein the loop formed around the portion of the rectum is a complete loop.

14. The bodily implant of claim 11, wherein the first extension member of the second support member is of a length capable of extending to a location located anteriorly to the anus of the patient.

15. The bodily implant of claim 11, wherein the second extension member of the second support member is of a length capable of extending to a location located posteriorly to the anus of the patient.

16. The bodily implant of claim 11, wherein the first support member includes a first extension member extending from a first terminal end portion of the first support member, the first support member including a second extension member extending from a second terminal end portion of the first support member.

17. The bodily implant of claim 11, wherein the first support member includes a first coupling portion disposed between a first terminal end portion and the first opening of the first support member and a second coupling portion disposed between a second terminal end portion and the second opening of the first support member, the second support member including a first coupling portion and a second coupling portion, the first coupling portion of the first support member being configured to be coupled to the first coupling portion of the second support member, the second coupling portion of the first support member being configured to be coupled to the second coupling portion of the second support member.

18. A method for placement of a bodily implant within a body of a patient, the method comprising:

placing a support member within the body of the patient;

coupling a first coupling portion of a first end of the support member with a second coupling portion of a second end of the support member wherein an inner surface of the support member is configured to form a complete loop around a portion of a rectum of a patient; and securing a mesh arm member that extends from an outer surface between the first end and the second end of the support member to a portion of the body of the patient to help retain the bodily implant in place within the body of the patient, the mesh arm member having a material that is the same as a material of the support member, the support member having a first lateral edge and a second lateral edge, the first and second lateral edges extending from the first end and the second end, the first and second lateral edges being parallel to a longitudinal axis of the support member, the mesh arm member extending from the first lateral edge to the second lateral edge along an axis perpendicular to the longitudinal axis.

* * * * *